United States Patent [19]
Valberg

[11] Patent Number: 5,584,823
[45] Date of Patent: Dec. 17, 1996

[54] ILLUMINATED EYE DROPPER DEVICE

[75] Inventor: John D. Valberg, Ottawa, Canada

[73] Assignee: Ontario Incorporated, Nepean, Canada

[21] Appl. No.: 504,960

[22] Filed: Jul. 20, 1995

[51] Int. Cl.⁶ .............................. A61M 35/00; B65D 5/66
[52] U.S. Cl. ............................ 604/294; 604/300; 222/113
[58] Field of Search ...................... 222/113, 183, 222/192, 206, 215, 420; 362/96, 101; 604/294, 295, 300

[56] References Cited

U.S. PATENT DOCUMENTS

| | | |
|---|---|---|
| 2,547,450 | 4/1951 | Du Pont . |
| 4,515,295 | 5/1985 | Dougherty ............................ 604/300 |
| 4,550,866 | 11/1985 | Moore . |
| 4,629,456 | 12/1986 | Edwards . |
| 5,133,702 | 7/1992 | Py ...................................... 604/302 |
| 5,307,249 | 4/1994 | Vanwynsberghe . |
| 5,321,591 | 6/1994 | Cimock et al. ...................... 362/186 |
| 5,387,202 | 2/1995 | Baron ................................. 604/300 |

FOREIGN PATENT DOCUMENTS

| | | |
|---|---|---|
| 180056 | 10/1917 | Canada . |
| 946348 | 4/1974 | Canada . |
| 1222991 | 6/1987 | Canada . |
| 2142829 | 1/1985 | United Kingdom . |

*Primary Examiner*—John G. Weiss
*Assistant Examiner*—David J. Cho
*Attorney, Agent, or Firm*—Dickstein Shapiro Morin & Oshinsky LLP

[57] ABSTRACT

There is provided a new and useful device to facilitate the dispensing of eye drops from a conventional translucent or transparent eye dropper bottle which has a drop-dispensing tip at one end, a bottom at the other end and resilient, squeezable sides between those ends to dispel the bottle contents. The device combines a light source and a holder to hold the eye dropper bottle in place relative to the light source so that light from the source will pass through the bottom of the bottle, when in use, to illuminate a droplet of the contents of the bottle being dispensed from the tip.

5 Claims, 2 Drawing Sheets

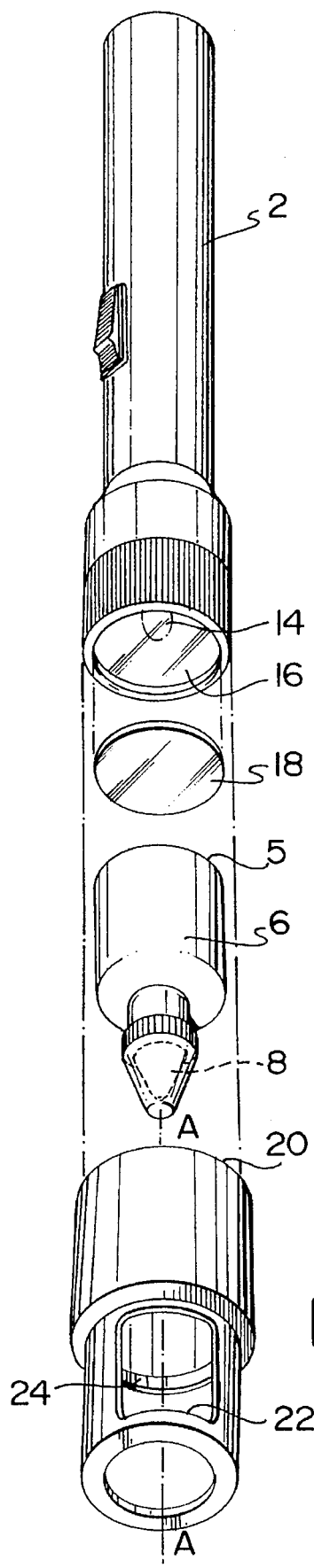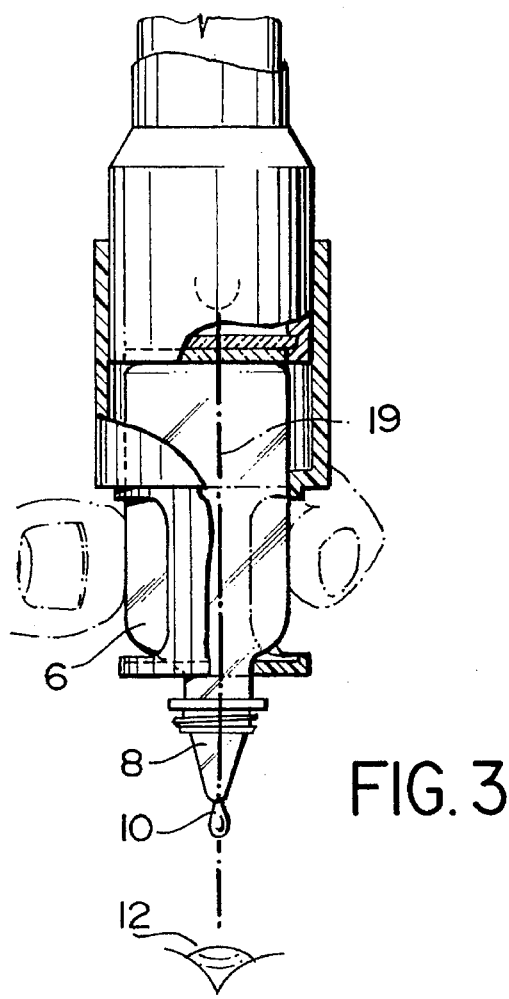
FIG. 2
FIG. 3

ILLUMINATED EYE DROPPER DEVICE

BACKGROUND OF THE INVENTION

The present invention relates to an improvement in the dispensing of eye drops frown a conventional eye dropper bottle. More particularly, tile invention discloses a convenient, easy-to-use device for assisting a patient administer eye drops while standing up or lying down and with or without ambient illumination.

The conventional eye dropper bottle is made of squeezable translucent or transparent plastic material and dispenses drops into tile patient's eye from an orifice located within a dispensing tip of the bottle. These bottles come in many different shapes and sizes. Further, the cap of the bottle is often of a defined color to readily indicate to the user which medication is contained within the bottle. The tip, however, is not itself colored because of concern for leaching.

When dispensing a drop from a bottle, it is imperative that the orifice be accurately positioned above the eye. The majority of tile medications being dispensed are extremely expensive and therefore, any spillage frown inaccurately dispensing a drop into the eye can be very costly to the patient. In addition, accurate insertion of a drop allows the patient to be certain about the placement and will prevent the patient from overdosing on the medication. While it is desirable to hold the tip in close proximity to the eye, contact with the eyelid, or other surfaces on the face or eye, may cause contamination of the tip of the bottle or injury to the patient.

Approximately 98% of all cataract surgery is performed on an out-patient basis. Thus, patients are often required to dispense eye drops at home, frequently without the aid of trained professionals, relatives or friends. However, for these patients, their sight and ability to gauge distances is typically adversely affected by the surgery, thus severely hampering their ability to use the conventional eye dropper bottle. An effective, easy to use dispenser aid with an increased ability to accentuate a drop being dispensed at the tip of the bottle would meet this need with reduced learning time for first time users, reduced complications and reduced waste.

Many of the devices for assisting in dispensing such drops, currently in use, do not provide a large enough target area, or do not illuminate and contrast the drop dispensing tip sufficiently to meet the needs of many of the patients. Nor do they minimize the risk of waste and contamination outlined above.

Canadian Patent No. 1,222,991 of Dougherty, issued Jun. 16, 1987 relates to a device for illuminating the dispensing tip of the conventional eye dropper bottle. It teaches a separate device mountable to the bottle which directs a beam of light, from a position beside the bottle, onto the dispensing tip of a tube attached to the tip of the bottle. However, the device requires that the dispensing tip be positioned at a significant distance from the actual bottle and from the patient's finger tips thus complicating its use. In addition, the target area provided by the illumination of Dougherty is not increased visually to any significant extent. The small illuminated tip and drop would make the device difficult to use for patients with macular degeneration and loss of central visual field.

U.S. Pat. No. 4,550,866 of Moore, issued Nov. 5, 1985 teaches a means of improving the visibility of the tip portion of a dispensing bottle by attaching a multi-colored tip on to the flange of the bottle to replace the existing tip. This requires handling by the patient and has the obvious problem of risking contamination of the medicine or the tip.

U.S. Pat. No. 4,629,456 of Edwards, issued Dec. 16, 1986 similarly teaches a device to be placed on the tip of the bottle necessitating the handling of the tip by the patient, in order to insert the device onto the tip of the bottle. The device is intended to improve the target area of the dispenser but makes no mention of illuminating the tip.

SUMMARY OF THE INVENTION

In one aspect of the present invention there is provided a device to facilitate the dispensing of eye drops from a conventional translucent or transparent eye dropper bottle which has a drop-dispensing tip at one end, a bottom at the other end and resilient, squeezable sides between those ends to dispel the bottle contents. The device consists of a light source and a holder to hold the eye dropper bottle in place relative to the light source so that light from the source will pass through the bottom of the bottle, when in use, to illuminate a droplet of the contents of the bottle being dispensed from the tip.

In another aspect of the present invention there is provided a sleeve to hold a conventional eye dropper bottle in place relative to a light source so that light passes through the bottom of the bottle to illuminate a droplet of fluid being dispensed from the tip.

In a preferred embodiment of the invention, the device further comprises a colored filter, positioned in the holder relative the light source so that light from the source will pass through the filter before it passes through tile bottom of tile bottle. The filter may be colored to correspond to the color of the cap of the eye dropper bottle.

In another preferred embodiment of the invention, the holder comprises a rigid, elongated sleeve, one end of which is open and provided with means to releasably secure the holder to the light source. The other end of the sleeve is open but constricted in such a way as to seatably engage a dispensing end of the bottle. The interior of the sleeve and the constricted end are constructed so as to firmly hold the bottle within the sleeve, with the dispensing tip extending frown the constricted end. The sleeve is provided with openings in its sides so as to permit squeezing of the sides of the bottle for dispensing fluid from the bottle.

The device of the present invention thus provides a means of facilitating and improving the dispensing of fluid from a conventional eye dropper bottle. A user positions the bottle relative the device's light source such that the beam of light passes through the bottom of the bottle and illuminates a droplet of fluid being dispensed frown the bottle. Thus, a patient using the device can more easily and accurately insert a drop of fluid into the eye, minimizing the risk of spillage and contamination. In addition, when filters are used, a visually handicapped patient would be able to identify the type of drop (by the color of the transilluminated bottle) if more than one type of drop was administered.

BRIEF DESCRIPTION OF THE DRAWINGS

These and other advantages of the invention will become apparent upon reading the following detailed description and upon referring to the drawings in which:

FIG. 2 is an exploded perspective view of the device.

FIG. 3 is a cross-sectional view taken along line A—A of FIG. 2.

Figure 1:
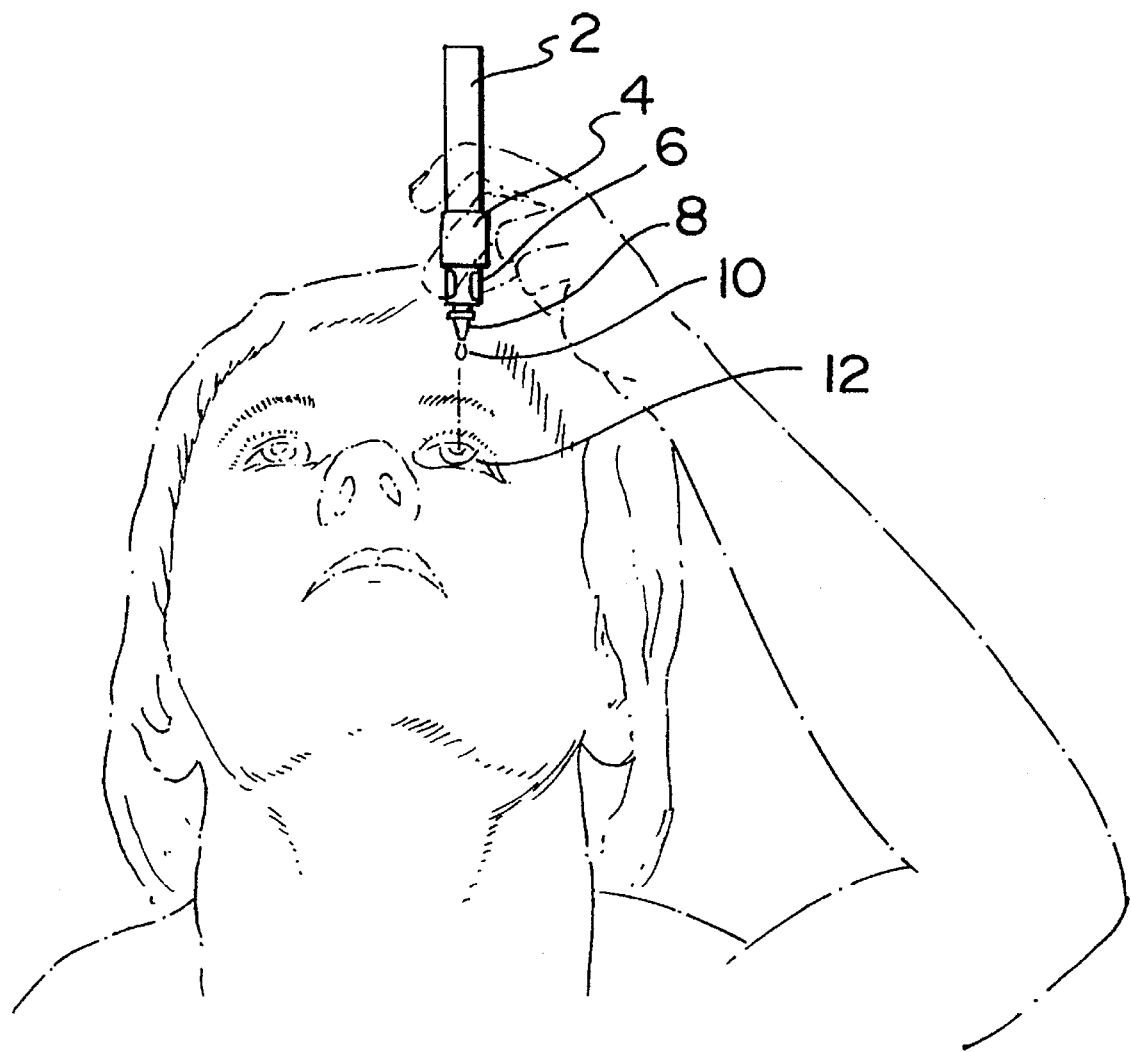
FIG. 1 is a perspective view of the device in use.

While the invention will be described in conjunction with illustrated embodiments, it will be understood that it is not intended to limit the invention to such embodiments. On the contrary, it is intended to cover all alternatives, modifications and equivalents as may be included within the spirit and scope of the invention as defined by the appended claims.

DETAILED DESCRIPTION OF THE INVENTION

In the following description, similar features in the drawings have been given similar reference numerals.

Turning to the drawings, FIG. 1 shows a perspective view of a light source 2 in combination with a sleeve 4 housing a conventional eye dropper bottle 6. The bottle 6 is shown dispensing from tip 8 a drop 10 of fluid into an eye 12 of a patient.

FIG. 2 shows an exploded view of the device. The light source 2, shown in this embodiment as a flashlight with bulb 14 and lens 16, is combined with a filter 18. In a preferred embodiment of the invention the filter may be color to correspond to the color of a cap (not illustrated) of the bottle 6 which color is used by the medical and pharmaceutical professions to indicate the type of medicine within the bottle. Thus, when the device is in use, a light beam as shown in FIG. 3 at 19 from the light source 2 will pass through the filter 18 and then pass through the bottom 5 of the bottle as colored light, corresponding to the medication within the bottle, to color the tip 8, drop 10 and the top of bottle 6.

The sleeve 4 is open at end 20 and configured at that end such that it is releasably securable to the light source 2. Where light source 2 is a flashlight, the sleeve is configured so that it an be releasably seated over lens 16 so as to secure in position bottles of varying heights. The other end 22 of the sleeve 4 is open but constricted so as to seatably engage the dispensing end of the bottle 6 with the dispensing tip 8 extending from that constricted end 22.

The sleeve 4 is further provided with openings 24 in the sides of the sleeve. These openings permit the user to grasp and squeeze the sides of the bottle, as shown in FIG. 3, to dispel a drop 10 of fluid into the eye 12. The drop 10 will be illuminated by the beam of light 19, and colored as a result of the filter 18, thus providing the patient with an illuminated, colored, and thus improved, target area about the dispensing tip 8. Such illumination and coloring provide greater visibility of drop 10, and hence greater accuracy to the patient in dispensing eye drops. As well, the illumination permits application of the medicine without ambient light. Thus, drops can be self-administered by a patient at night, in an otherwise dark room, while lying in bed before going to sleep, a time when the application of such drops is frequently required.

Thus, it is apparent that there has been provided in accordance with the invention ILLUMINATED EYE DROPPER DEVICE that hilly satisfies the objects, aims and advantages set forth above. While the invention has been described in conjunction with illustrated embodiments thereof, it is evident that many alternatives, modifications and variations will be apparent to those skilled in tile art in light of tile foregoing description. Accordingly, it is intended to embrace all such alternatives, modifications and variations as fall within the spirit and broad scope of the invention.

The embodiments of the invention in which an exclusive property or privilege is claimed are defined as follows:

1. A device to facilitate the dispensing of eye drops from a conventional translucent or transparent eye dropper bottle having a drop-dispensing tip at one end, a bottom at the other end and resilient, squeezable sides between those ends to dispel the bottle contents, in drop form, from the dispensing tip, the device comprising:

(a) a light source
    (b) a holder constructed so as to be secured to the light source to hold the eye dropper bottle in place relative to the light source with said drop-dispensing tip clear of said holder and oriented away from the light source so that light from the source will pass through the bottom of the bottle, when in use, to illuminate a droplet of said contents being dispensed from the tip.

2. A device according to claim 1 further comprising a colored filter positioned in said holder so that light from the source will pass through the filter before it passes through the bottle bottom.

3. A device according to claim 2 wherein the filter is colored to correspond to a color of a cap of the eye dropper bottle.

4. A device according to claim 1 wherein the holder comprises a rigid, elongated sleeve, one end of which is open and provided with means to releasably secure the holder to the light source, the other end of which is open but constricted so as to seatably engage a dispensing end of the bottle, the interior of the sleeve and the constricted end constructed so as to firmly hold the bottle within the sleeve, with the dispensing tip extending from the constricted end.

5. A device according to claim 4 wherein the sleeve is provided with openings in its sides so as to permit squeezing of the sides of the bottle for dispensing of fluid from the bottle.

\* \* \* \* \*